United States Patent
Putaala et al.

(10) Patent No.: US 12,419,923 B2
(45) Date of Patent: Sep. 23, 2025

(54) BACTERIA

(71) Applicant: DUPONT NUTRITION BIOSCIENCES APS, Kongens Lyngby (DK)

(72) Inventors: Heli Putaala, Kotka (FI); Sofia Forssten, Kotka (FI); Sampo Lahtinen, Kotka (FI); Arthur Ouwehand, Kotka (FI); Jaana Mättö, Helsinki (FI); Harri Mäkivuokko, Helsinki (FI); Janne Nikkilä, Helsinki (FI)

(73) Assignee: INTERNATIONAL N&HDENMARK APS, Kongens Lyngby (DK)

( * ) Notice: Subject to any disclaimer, the term of this patent is extended or adjusted under 35 U.S.C. 154(b) by 0 days.

(21) Appl. No.: 18/364,151

(22) Filed: Aug. 2, 2023

(65) Prior Publication Data

US 2024/0245735 A1   Jul. 25, 2024

Related U.S. Application Data

(63) Continuation of application No. 16/333,770, filed as application No. PCT/EP2017/072859 on Sep. 12, 2017, now abandoned.

(30) Foreign Application Priority Data

Sep. 16, 2016  (EP) .................................. 16189291

(51) Int. Cl.
| | |
|---|---|
| A61K 35/747 | (2015.01) |
| A23L 33/00 | (2016.01) |
| A23L 33/135 | (2016.01) |
| A61K 35/745 | (2015.01) |
| A61P 1/04 | (2006.01) |
| A61P 1/12 | (2006.01) |
| A61P 1/14 | (2006.01) |

(52) U.S. Cl.
CPC .......... *A61K 35/747* (2013.01); *A23L 33/135* (2016.08); *A23L 33/30* (2016.08); *A61K 35/745* (2013.01); *A61P 1/04* (2018.01); *A61P 1/12* (2018.01); *A61P 1/14* (2018.01)

(58) Field of Classification Search
None
See application file for complete search history.

(56) References Cited

U.S. PATENT DOCUMENTS

| | | |
|---|---|---|
| 5,540,924 A | 7/1996 | Onishi et al. |
| 2004/0115179 A1 | 6/2004 | Liu et al. |
| 2007/0248582 A1 | 10/2007 | Luquet |
| 2008/0160565 A1 | 7/2008 | Saito et al. |
| 2012/0276201 A1 | 11/2012 | Trachtman |
| 2022/0354908 A1 | 11/2022 | Putaala et al. |

FOREIGN PATENT DOCUMENTS

| | | | |
|---|---|---|---|
| CA | 2588940 A1 | 6/2006 | |
| EP | 1880726 A1 | 1/2008 | |
| WO | 2011/154616 A2 | 12/2011 | |
| WO | 2018/050650 A1 | 3/2018 | |
| WO | WO-2018050623 A1 * | 3/2018 | ........... A23L 33/135 |

OTHER PUBLICATIONS

Anglenius, et al., Microorganisms, vol. 11, 329, pp. 1-22 (2023).
Boren, et al., Science, vol. 262, pp. 1892-1895 (1993).
Corcoran, Applied and Environmental Microbiology, vol. 71(6), pp. 3060-3067 (2005).
Ding, et al., Journal of Food Science, vol. 72(9), pp. M446-M450 (2007).
Imberty, et al., Current Opinion in structural Biology, vol. 18, pp. 567-576 (2008).
International Search Report for PCT/EP2017/072859 (mailed Nov. 6, 2017).
International Preliminary Report on Patentability for PCT/EP2017/072859 (issued Mar. 19, 2019).
JCM Catalogue, Lactobacillus crispatus, T. Fujisawa F199 (printed 2023; citing accessioned date of 1993).
Kimoto, et al., Letters in Applied Microbiology, vol. 29, pp. 313-316 (1999).
Liong, et al., Journal of Dairy Science, vol. 88, pp. 55-66 (2005).
Makivuokko, et al., BMC Microbiology, vol. 12, 94, pp. 1-22 (2012).
Martens, et al., Cell Host & Microbe, vol. 4, pp. 447-457 (2008).
Pisano, et al., Biomed Research International, vol. 2014, pp. 1-9 (2014).
Saarela, et al., Journal of Applied Microbiology, vol. 106, pp. 1204-1212 (2009).
Uchida, et al., Bioscience, Biotechnology, and Biochemistry, vol. 68(5), pp. 1004-1010 (2004).
Uchida et al., Research in Microbiology, vol. 157(7), pp. 659-665 (2006).
Xiao, et al., Applied and Environmental Microbiology, vol. 76(1), pp. 54-59 (2010).
Non-final Office action in U.S. Appl. No. 16/332,912 (Jul. 19, 2021).
Non-final Office action in U.S. Appl. No. 17/579,006 (Oct. 9, 2024).

* cited by examiner

*Primary Examiner* — Blaine Lankford

(57) ABSTRACT

The present invention relates to bacteria and metabolites thereof that are capable of binding to A, B and/or O blood type antigens or which are acid and/or bile tolerant, their use in probiotic compositions and food products, and methods for their selection. The invention also relates to the use of said bacteria and metabolites for the prevention and/or treatment of gastrointestinal disorders.

10 Claims, No Drawings

BACTERIA

FIELD OF THE INVENTION

The present invention relates to novel bacteria and metabolites thereof, their use in probiotic compositions and food products, methods for selection of probiotic bacteria and methods of personalising a probiotic composition or food product. The invention also relates to the use of said bacteria, metabolites and compositions for the prevention and/or treatment of gastrointestinal disorders.

BACKGROUND

The human body is colonised with a myriad of microbes representing over 1000 bacterial species. The composition and density of the microbiota is specific for each body location. The majority of the bacterial biomass resides in the gastrointestinal tract (GIT), especially in the lumen of the large intestine, where two populations are present, the lumen and mucosa-associated populations that differ from each other. The microbiota has an important role in human health. It contributes to the maturation of the gut tissue, to host nutrition, pathogen resistance, epithelial cell proliferation, host energy metabolism and immune response. An altered composition and diversity of the GIT microbiota have been associated with several diseases, such as inflammatory bowel disease (IBD), irritable bowel syndrome (IBS), rheumatoid arthritis, atopic eczema, asthma and type 1 diabetes.

The microbiota of adults is fairly stable over time and unique within an individual. The similarity of the dominant microbial population is higher in monozygotic twins compared to unrelated subject suggesting the role of host genetic factors on the microbiota composition. Some animal studies suggest that the major histocompatibility complex is involved in the genetic regulation of gut microbiota. However, little is known about which genes or other factors determine or regulate the spectrum of microbial composition.

The mucosal layer covering the gut epithelium has an important role as the first layer of host defenses, but it also enables contacts between intestinal microbiota and the host. The mucus is mainly composed of mucins, large glycoproteins containing a protein core and attached oligosaccharides. Although the mucus layer prevents the direct contact of the bacteria with the epithelial cells in the colon, it provides adhesion sites for the GIT bacteria and has thus an important role in bacterial colonization. Besides adhesion sites, the secreted mucus provides endogenous substrate for bacteria. The mucus may be a major nutrient source in situations, where carbohydrates originating elsewhere are limited.

Blood group antigens are attached to various components in the red blood cell membrane, and the antigens expressed on the red blood cell determine an individual's blood group. The main two blood groups are called ABO (with blood types A, B, AB, and O) and Rh (with Rh D-positive or Rh D-negative blood types). ABO blood group antigens are expressed in the mucus of secretor type individuals (roughly 80% of Western population). The expression of the ABO antigens is site-specific. For example, in the GIT the expression of fucosylated glycans including ABO blood group antigens decreases towards the distal parts of the intestine. Some microbes, such as *Helicobacter pylori* and some other pathogenic bacteria and viruses, have been shown to use ABO blood group antigens as adhesion receptors (Boren et al. 1993, Imberty and Varrot 2008). ABO antigen binding ability has been reported also for *Lactobacillus* spp., which tend to adhere in a strain-specific manner (Uchida et al. 2006). Bifidobacteria and *Bacteroides thetaiotaomicron* are, for example, also able to specifically utilize blood group antigens, e.g. the glycan structures of ABO antigens (Martens et al. 2008, Xiao et al. 2010). The ABO blood group status of an individual also has an effect on the relative proportions of the host microbiota (Mäkivuokko et al. 2012).

Many probiotic supplements and microbiota modulation products currently available on the market are ineffective in promoting the desired health effects for every individual and effect commonly varies from person to person. Thus, there is a continuous need for more specific or personally tailored products that are able to mediate the health effects more efficiently.

SUMMARY OF THE INVENTION

The present invention is based on the inventors' surprising discovery that certain bacterial strains showed enhanced in vitro adhesion to one or more of the ABO blood group antigens. This finding enables the selection of ABO blood group-specific bacteria for use in probiotic compositions and for the treatment or prevention of gastrointestinal disorders.

While not wishing to be bound by theory, it is thought that as the glycan structures of the ABO blood groups are abundant in the mucosa and serve as bacterial adhesion sites and nutrient sources, stronger binding to one or more ABO antigens by a probiotic bacterium will improve its colonization of the bacterium in the gastrointestinal tract by enhancing its interaction with the mucosa. The probiotic bacterium may also demonstrate enhanced health effects by blocking the adhesion and invasion of certain pathogenic microbes which also bind to ABO antigens. A probiotic bacterium which adheres to an ABO antigen could also enhance the probiotic responses by providing tighter and longer-lasting contact between the host cells and probiotics. It could further provide the host easier access to any beneficial metabolites produced by the probiotics when probiotics are colonized tighter and more long-lasting.

The inventors have further shown that certain probiotic bacteria are more resistant to acid and/or bile. These properties may be helpful to enable the bacterium or metabolite thereof to survive the conditions of the stomach and gastrointestinal tract, and are therefore advantageous properties for a probiotic bacterium. Acid tolerance may also be beneficial if the strain is fermented in a product such as yogurt.

Accordingly the present invention provides a bacterium or metabolite thereof characterised by:
 a) an average A antigen adhesion of more than 100% when compared to *L. crispatus* LMG18199; and/or
 b) an average B antigen adhesion of more than 100% when compared to *L. crispatus* LMG18199; and/or
 c) an average O antigen adhesion of more than 100% when compared to *L. crispatus* LMG18199; and/or
 d) more than −2.6 average acid tolerance represented as a log change when measured at pH 2.5 for 1.5 hours as defined in an acid resistance assay; and/or e) more than 40% average bile tolerance represented as growth in 0.9% dehydrated fresh bile as a percentage of growth in MRS without bile as defined in a bile resistance assay.

The bacterium of the invention may be a bacterial strain deposited as DSM 32111, DSM 32108, DSM 32107, DSM 32098, DSM 32104, DSM 32112, DSM 32109, DSM 32105, DSM 32110, DSM 32103, DSM 32099, DSM 32106, DSM 32097, DSM 32114, DSM 32115 or a mutant, a variant and/or a progeny thereof.

According to another aspect of the present invention there is provided a probiotic composition comprising a bacterium or metabolite thereof according to the invention and a suitable carrier.

The probiotic composition of the invention may comprise a combination of 2, 3, 4, 5 or 6 bacterial strains or metabolites thereof according to the invention, optionally in combination with one or more further bacterial strains.

The probiotic composition may further comprise a prebiotic component.

The present invention also provides a method of producing a probiotic composition of the invention, the method comprising combining the selected bacterium or metabolite thereof with a suitable carrier.

The invention further provides a food product comprising a probiotic composition according to the invention.

According to another aspect of the invention there is provided a method of selecting a bacterium or metabolite thereof comprising:
  a) admixing one or more test bacteria with an A antigen, B antigen, O antigen or combinations thereof;
  b) admixing one or more *Lactobacillus reuteri* RC-14 control bacteria with A antigen, B antigen, O antigen or combinations thereof;
  c) incubating said admixtures of step a) and b);
  d) comparing the affinity of adhesion to said A antigen, B antigen, O antigen or combinations thereof of the test bacteria and *Lactobacillus reuteri* RC-14; and
  e) selecting bacteria having a higher affinity of adhesion to said A antigen, B antigen, O antigen or combinations thereof than *Lactobacillus reuteri* RC-14.

In one embodiment, the admixtures are incubated in separate vials in step (b).

In another embodiment, the method is a fluorescence based method.

In a further embodiment, bacteria are selected which have:
  a) an average A antigen adhesion intensity of fluorescence of more than 549;
  b) an average B antigen adhesion intensity of fluorescence of more than 519; and/or
  c) an average O antigen adhesion intensity of fluorescence of more than 746.

The invention further provides a bacterium or metabolite thereof selected by the method of the invention.

In a further aspect, the invention provides the use of a bacterium or metabolite of the invention or selected by a method of the invention, or a probiotic composition of the invention, for the manufacture of a formulation for preventing and/or treating gastrointestinal disorders.

The invention also provides a bacterium or metabolite of the invention or selected by a method of the invention, or a probiotic composition of the invention, for use in preventing and/or treating gastrointestinal disorders.

In another aspect, the invention provides a method of preventing and/or treating gastrointestinal disorders comprising administering to a subject a bacterium or metabolite thereof according to the invention or selected by a method of the invention, or a probiotic composition of the invention, in a pharmaceutically effective amount.

DETAILED DESCRIPTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure which can be had by reference to the specification as a whole. Accordingly, the terms defined immediately below are more fully defined by reference to the specification as a whole.

Other definitions of terms may appear throughout the specification. Before the exemplary embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that such publications constitute prior art to the claims appended hereto.

It will be understood that in the following, preferred embodiments referred to in relation to one broad aspect of the invention are equally applicable to each of the other broad aspects of the present invention described herein. It will be further understood that, unless the context dictates otherwise, the preferred embodiments described herein may be combined.

The term "bacterium" or "bacterial" is used herein to refer to any bacterial species, strains or combinations thereof, and is not limited to strains currently accepted as probiotics. However, bacterial strains used in the present invention are those that a suitable for human and/or animal consumption. A skilled person will be readily aware of specific species and or strains from within the genera described herein which are used in the food and/or agricultural industries and which are generally considered suitable for human and/or animal consumption. Such bacterial strains are typically non-pathogenic, and may be generally regarded as safe for human use (e.g. GRAS).

The term "bacterium" is generally used to refer to whole bacteria, for example whole viable bacteria.

Bacteria suitable for use in the present invention include, but are not limited to, *Bifidobacterium, Brevibacterium, Propionibacterium, Lactococcus, Streptococcus, Lactobacillus, Enterococcus, Pediococcus, Leuconostoc* and/or *Oenococcus*.

In one embodiment the bacterium belongs to the genus *Lactobacillus*. Suitable strains of *Lactobacillus* include *L. acidophilus, L. amylovorus, L. brevis, L. casei, L. crispatus, L. fermentum, L. vaginalis, L. curvatis, L. delbrueckii bulgaricus, L. gasseri, L. helveticus, L. jensenii, L. mucosae, L. paracasei, L. plantarum, L. rhamnosus, L. silvarius* and *L. ruminis*.

In a further aspect, the present invention provides the novel bacterial strains DGCC11884, DGCC11864, DGCC11860, DGCC11873, DGCC11852, DGCC11853, DGCC11865, DGCC1925, DGCC11866, DGCC5111, DGCC11854, DGCC11858, DGCC11887, DGCC11862 and DGCC11881. These strains have been deposited by DuPont Nutrition Biosciences ApS, Langebrogade 1, P.O. Box 17, DK-1001 Copenhagen K, under the Budapest Treaty on the International Recognition of the Deposit of Microorganisms for the purposes of Patent Procedure at Leibniz Institute DSMZ-German Collection of Microorganisms and Cell Cultures, Inhoffenstr. 7 B, D-38124 Braunschweig on 29 Jul. 2015 under accession numbers DSM 32111, DSM 32108, DSM 32107, DSM 32098, DSM 32104, DSM 32112, DSM 32109, DSM 32105, DSM 32110, DSM 32103, DSM 32099, DSM 32106, DSM 32097, DSM 32114, DSM 32115.

We hereby confirm that the depositor has authorised the applicant to refer to the deposited biological material in this application and has given his unreserved and irrevocable consent to the deposited material being made available to the public.

The invention further provides a mutant, a variant and/or a progeny of the deposited bacterial strains.

As used herein, the term "mutant" refers to any microorganism resulting from modification of the parent (i.e. deposited) strain. For example, a mutant may be a microorganism resulting from genetically modifying a deposited strain.

As used herein, the term "variant" refers to a naturally occurring microorganism which is derived from the parent (i.e. deposited strain). For example, a variant may be a microorganism resulting from adaption to particular cell culture conditions.

As used herein, the term "progeny" means any microorganism resulting from the reproduction or multiplication of any one of the deposited strains. Therefore, "progeny" means any direct descendant of any one of the deposited strains. As such, the progeny strain may itself be identified as the same strain as the parent (i.e. deposited) strain. It will be apparent to one skilled in the art that due to the process of asexual reproduction, a progeny strain will be genetically virtually identical to the parent strain. Accordingly, in one embodiment, the progeny may be genetically identical to the parent strain, and may be considered to be a "clone" of the parent strain. Alternatively, the progeny may be substantially genetically identical to the parent strain.

The mutant, variant or progeny may have at least 90, 95, 98, 99, 99.5 or 99.9% sequence identity over the entire length of the bacterial genome with their parent strain. Furthermore, the mutant, variant or progeny will retain the same phenotype as the deposited parent strain, for example the mutant or variant may demonstrate the same or equivalent level of in vitro adhesion to A, B and/or O blood type antigen as the parent strain.

As used herein, the term "metabolite" refers to all molecules produced or modified by the bacteria as a result of bacterial metabolism during growth, survival, persistence, transit or existence of bacteria during probiotic product manufacture and storage and during gastrointestinal transit in a mammal. Examples include all organic acids, inorganic acids, bases, proteins and peptides, enzymes and co-enzymes, amino acids and nucleic acids, carbohydrates, lipids, glycoproteins, lipoproteins, glycolipids, vitamins, all bioactive compounds, metabolites containing an inorganic component, and all small molecules, for example nitrous molecules or molecules containing a sulphurous acid.

A metabolite or metabolites are typically obtained from the supernatant of a cell culture from which the bacterial cells have been removed. In one embodiment, the cells may be grown in MRS medium under anaerobic conditions for 6-24 hours at 37° C. According to a further embodiment, the bacterial cell culture may be grown to a cell density of at least about $OD_{600}$ 0.5, 1.0, 1.5, 2.0, 2.5, or 3.0, for example from 1.5 to 2.5 $OD_{600}$. The cells may suitably be removed by centrifugation or by filtration. It will be apparent that the supernatant may be used directly in the formulations of the present invention, or that one or more of the metabolites may be isolated from the supernatant by any suitable means prior to use.

Suitable metabolites for use in the present invention include, but are not limited to, metabolites from any of the above mentioned bacteria.

According to the present invention, the bacterium or metabolite thereof is characterised by its adhesion to a particular ABO blood type antigen, with reference to a control strain. The adhesion to the antigen may be measured by mixing the bacterium or metabolite thereof with the antigen, and measuring adhesion according to any suitable test or assay. In one embodiment, the method is a fluorescence-based method. For example, the blood group antigen may be biotinylated and combined with a sample of bacteria to be tested, then transferred to streptavidin coated plates and the attached bacteria detected with a suitable dye, such as a fluorescent dye. Antigen may be bound to any immobilized matrix for affinity binding assays and the binding of bacteria to it could be detected using suitable antibodies, fluorometric or colorimetric stains, or by labelling the bacteria with any labelling technique such as radioactive labelling. It could be done the other way around, by attaching bacterial components to immobilized matrix, and by investigating if the blood group antigens can bind.

According to one aspect of the invention, the antigen adhesion is compared to *Lactobacillus crispatus* LMG18199 (available from BCCM/LMG collection). According to another aspect of the invention, the antigen adhesion is compared to *Lactobacillus reuteri* RC-14 (available from Christian Hansen A/S, Denmark).

According to another aspect of the present invention, the bacterium or metabolite thereof is selected on the basis of its resistance to bile and/or acid. These properties may be helpful to enable the bacterium or metabolite thereof to survive the conditions of the stomach and gastrointestinal tract, and are therefore advantageous properties for a probiotic bacterium.

Any suitable bile resistance assay may be used to determine average bile tolerance. In one embodiment, the bile resistance assay comprises incubating strain cultures in culture medium (e.g. MRS) containing a defined amount of dehydrated fresh bile (e.g. oxgall, available under the brand name Difco™ from BD), such as 0.9% or 0.3% at 37° C. for 24 hours in anaerobic conditions. Growth is measured before and after incubation and the bile tolerance results are expressed as % growth (OD) with bile in comparison to growth without bile.

Any suitable acid resistance assay may be used to determine average acid tolerance. In one embodiment, the acid tolerance assay comprises incubating bacterial cells in suitable medium (e.g. PBS) at neutral pH (i.e. pH 7.2) levels and at a comparator acidic pH (such as pH 2.5 or pH 3.5) for at least 90 min at 37° C. The ten-fold dilution series are grown on MRS agar, and colonies are counted after 48 h incubation in anaerobic conditions at 37° C. The results for acid tolerance are expressed as growth log reduction of CFU after exposure to acid conditions in comparison to neutral pH.

In a preferred embodiment, the bacterium or metabolite thereof is characterised by both its adhesion to a particular ABO blood type antigen, with reference to a control strain, and by its acid and/or bile tolerance. Accordingly, the invention provides a bacterium or metabolite thereof characterised by:
  a) an average A, B and/or O antigen adhesion of more than 100% when compared to *L. crispatus* LMG18199; and
  b) more than −2.6 average acid tolerance represented as a log change when measured at pH 2.5 for 1.5 hours as defined in an acid resistance assay and/or more than 40% average bile tolerance represented as growth in 0.9% dehydrated fresh bile as a percentage of growth in MRS without bile as defined in a bile resistance assay.

The invention further provides a probiotic composition comprising one or more bacterial strains that have been selected according to methods of the invention. The composition may comprise a single strain, or a combination of 2, 3, 4, 5, 6, 7, 8, 9 or 10 strains of the invention. The probiotic composition may further comprise additional strains, for example commercially available probiotic bacterial strains.

According to one embodiment, the probiotic composition of the invention further comprises one or more further bacterial strains.

In some embodiments the further micro-organism may be a bacterium from one or more of the following genera: *Lactococcus, Streptococcus, Pediococcus, Enterococcus, Leuconostoc, Carnobacterium, Propionibacterium, Bifidobacterium, Lactobacillus, Brevibacterium*, and *Vagococcus*. In one preferred embodiment the at least one further probiotic microorganism is selected from the genera *Lactobacillus, Streptococcus, Enterococcus, Bifidobacterium* and *Saccharomyces*.

In preferred embodiments, the further probiotic microorganism is a bacterium preferably a probiotic lactic acid bacterium and/or a probiotic *Bifidobacterium*. In one embodiment preferably the further microorganism is from the genus *Lactobacillus* or the genus *Bifidobacterium* or is a mixture thereof. Suitably, the microorganism may be a strain from the species *L. acidophilus, L. curvatus, L. rhamnosus, L. casei, L. paracasei, L. salivarius, B. lactis. B animalis, B. longum* and/or *B. bifidum*. In one embodiment, preferably the microorganism may be a strain from the species *L. acidophilus, L. curvatus, L. salivarius* and/or *B. lactis*.

The bifidobacterium may be any bifidobacterium having a probiotic effect, typically strains belonging to the species *Bifidobacterium animalis, Bifidobacterium breve, Bifidobacterium infantis, Bifidobacterium lactis, Bifidobacterium longum, Bifidobacterium bifidum* and *Bifidobacterium adolescentis* are used.

The *Lactobacillus* bacterium may be any of the following: *Lactobacillus acidophilus, Lactobacillus amylovorus, Lactobacillus bulgaricus, Lactobacillus casei, Lactobacillus delbrueckii, Lactobacillus fermentum, Lactobacillus gasseri, Lactobacillus helveticus, Lactobacillus johnsonii, Lactobacillus lactis, Lactobacillus paracasei, Lactobacillus pentosaceus, Lactobacillus plantarum, Lactobacillus reuteri, Lactobacillus rhamnosus*, and *Lactobacillus salivarius,*

According to one embodiment, the probiotic composition of the invention further comprises one or more, such as a combination of 2, 3, 4 or 5 of the following commercially available strains: *Lactobacillus acidophilus* NCFM; *Bifidobacterium lactis* BL-04; *Lactobacillus paracasei* LPC37; *Bifidobacterium lactis* HN019, and/or *Bifidobacterium lactis* Bi-07.

As used herein, the term "probiotic" refers to a live microorganism which, when administered in adequate amounts, confers a health benefit on the recipient. They are suitable for human consumption and therefore are non-pathogenic and non-toxic. These probiotic strains generally have the ability to survive the passage through the upper part of the digestive tract. Probiotic bacteria typically exercise their beneficial effect on health on the one hand via ecological interactions with the resident flora in the digestive tract, and on the other hand via their ability to influence the immune system in a positive manner via the "GALT" (gut-associated lymphoid tissue). Probiotic bacteria, when given in a sufficient number, have the ability to progress live through the intestine. However they do not cross the intestinal barrier and their primary effects are therefore induced in the lumen and/or the wall of the gastrointestinal tract. They then form part of the resident flora during the administration period. This colonization (or transient colonization) allows the probiotic bacteria to exercise a beneficial effect, such as the repression of potentially pathogenic microorganisms present in the flora and interactions with the immune system of the intestine.

While there are no lower or upper limits for probiotic use, it has been suggested that at least $10^6$-$10^{12}$, such as at least $10^6$-$10^{10}$, for example $10^8$-$10^9$ cfu as a daily dose may be effective to achieve the desired health effects in a subject. Accordingly, the probiotic bacteria used in accordance with the present invention may comprise from $10^6$ to $10^{12}$ CFU of bacteria/g of support, and more particularly from $10^8$ to $10^{12}$ CFU of bacteria/g of support, typically $10^9$ to $10^{12}$ CFU/g for the lyophilized form.

Suitably, the bacterium may be administered at a dosage of from about $10^6$ to about $10^{12}$ CFU of microorganism/dose, typically about $10^8$ to about $10^{12}$ CFU of microorganism/dose. By the term "per dose" it is meant that this amount of microorganism is provided to a subject either per day or per intake, typically per day. For example, if the microorganism is to be administered in a food product (for example in a yoghurt)—then the yoghurt will typically contain from about $10^8$ to $10^{12}$ CFU of the microorganism. Alternatively, however, this amount of microorganism may be split into multiple administrations each consisting of a smaller amount of microbial loading—so long as the overall amount of microorganism received by the subject in any specific time (for instance each 24 hour period) is from about $10^6$ to about $10^{12}$ CFU of microorganism, such as about $10^8$ to about $10^{12}$ CFU of microorganism.

In accordance with the present invention an effective amount of at least one strain of a microorganism may be at least $10^6$ CFU of microorganism/dose, for example from about $10^6$ to about $10^{12}$ CFU of microorganism/dose, such as about $10^8$ to about $10^{12}$ CFU of microorganism/dose.

CFU stands for "colony-forming units". By 'support' is meant the food product, dietary supplement or the pharmaceutically acceptable support or carrier.

While it is possible to administer the bacterium or metabolite alone according to the present invention (i.e. without any support, diluent or excipient), they are typically administered on or in a carrier or support as part of a product, in particular as a component of a food product, a dietary supplement or a pharmaceutical formulation. These products typically contain additional components well known to those skilled in the art.

Any product which can benefit from the composition may be used in the present invention. These include but are not limited to foods, particularly fruit conserves and dairy foods and dairy food-derived products, and pharmaceutical products.

The bacterial composition of the present invention may be formulated as a nutritional supplement. The bacterial composition may be in the form of, for example, a capsule, tablet, powder or emulsion.

A typical probiotic ingredient is a freeze-dried powder containing, for example, $10^{10}$-$10^{12}$ viable probiotic bacterial cells per gram. The powder may further comprise a suitable carrier, such as skim milk or sugars, typically oligosaccharides such as sucrose or trehalose.

Alternatively, the bacterial composition may be encapsulated using a carrier such as alginate, starch or xanthan. A typical capsule preparation may contain approximately $10^9$-$10^{11}$ viable probiotic bacterial cells per capsule.

The probiotic composition of the present invention may additionally contain one or more prebiotics. The term "prebiotic component" as used herein refers to any compound, nutrient or additional microorganism used to support or enhance a desired probiotic health effect or to assist the growth and/or activity of probiotic bacteria. Typically, prebiotics are carbohydrates (such as oligosaccharides), but the definition does not preclude non-carbohydrates. The most prevalent forms of prebiotics are nutritionally classed as soluble fibre. To some extent, many forms of dietary fibre exhibit some level of prebiotic effect.

In one embodiment, a prebiotic is a selectively fermented ingredient that allows specific changes, both in the composition and/or activity in the gastrointestinal microflora that confers benefits upon host well-being and health.

Suitably, the prebiotic may be used according to the present invention in an amount of 0.01 to 100 g/day, such as 0.1 to 50 g/day, or 0.5 to 20 g/day. In one embodiment, the prebiotic may be used according to the present invention in an amount of 1 to 10 g/day, such as 2 to 9 g/day, or 3 to 8 g/day. In another embodiment, the prebiotic may be used according to the present invention in an amount of 5 to 50 g/day, such as 10 to 25 g/day.

Examples of dietary sources of prebiotics include soybeans, inulin sources (such as Jerusalem artichoke, jicama, and chicory root), raw oats, unrefined wheat, unrefined barley and yacon.

Examples of suitable prebiotics include alginate, xanthan, pectin, locust bean gum (LBG), inulin, guar gum, galacto-oligosaccharide (GOS), fructo-oligosaccharide (FOS), polydextrose (i.e. Litesse®), lactitol, lactosucrose, soybean oligosaccharides, isomaltulose (Palatinose™), isomalto-oligosaccharides, gluco-oligosaccharides, xylo-oligosaccharides, manno-oligosaccharides, beta-glucans, cellobiose, raffinose, gentiobiose, melibiose, xylobiose, cyclodextrins, isomaltose, trehalose, stachyose, panose, pullulan, verbascose, galactomannans, and all forms of resistant starches. A particularly preferred example of a prebiotic is polydextrose.

The probiotic composition of the present invention may be used as, or in the preparation of, a food product. Herein, the term "food" is used in a broad sense and covers food for humans as well as food for animals (i.e. a feed). In one aspect, the food is for human consumption.

The food may be in the form of a solution or as a solid—depending on the use and/or the mode of application and/or the mode of administration.

A typical probiotic food product may contain approximately $10^9$-$10^{11}$ viable probiotic bacterial cells per daily dose. The probiotic bacteria may be incorporated in the food product as a probiotic ingredient, such as a freeze-dried powder, or may be cultured in the product.

When used as or in the preparation of a food, such as functional food, the composition of the present invention may be used in conjunction with one or more of: a nutritionally acceptable carrier, a nutritionally acceptable diluent, a nutritionally acceptable excipient, a nutritionally acceptable adjuvant, and a nutritionally active ingredient.

By way of example, the probiotic composition of the present invention can be used as an ingredient in soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The probiotic composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

The term "dairy product" as used herein is meant to include a medium comprising milk of animal and/or vegetable origin. As milk of animal origin there can be mentioned cow's, sheep's, goat's or buffalo's milk. As milk of vegetable origin there can be mentioned any fermentable substance of vegetable origin which can be used according to the invention, in particular originating from soybeans, rice or cereals.

According to one particular aspect, the food product employed according to the invention is a fermented milk or humanized milk.

For certain aspects, the present invention may be used in connection with yoghurt production, such as fermented yoghurt drink, yoghurt, drinking yoghurt, cheese, fermented cream, milk based desserts and others.

Suitably, the composition can be further used as an ingredient in one or more of cheese applications, meat applications, or applications comprising protective cultures.

The present invention also provides a method of preparing a food or a food ingredient, the method comprising admixing the composition according to the present invention with another food ingredient.

Advantageously, the present invention relates to products that have been contacted with the probiotic composition of the present invention (and optionally with other components/ingredients), wherein the composition is used in an amount to be capable of improving the nutrition and/or health benefits of the product.

As used herein the term "contacted" refers to the indirect or direct application of the composition of the present invention to the product. Examples of the application methods which may be used, include, but are not limited to, treating the product in a material comprising the composition, direct application by mixing the composition with the product, spraying the composition onto the product surface or dipping the product into a preparation of the composition.

Where the product of the invention is a foodstuff, the composition of the present invention is typically admixed with the product. Alternatively, the composition may be included in the emulsion or raw ingredients of a foodstuff. In a further alternative, the composition may be applied as a seasoning, glaze, colorant mixture, and the like.

For some applications, it is important that the composition is made available on or to the surface of a product to be affected/treated. This allows the composition to impart one or more of the following favourable characteristics: nutrition and/or health benefits.

The compositions of the present invention may be applied to intersperse, coat and/or impregnate a product with a controlled amount of a microorganism.

In one embodiment, the composition is used to ferment milk or sucrose fortified milk or lactic media with sucrose and/or maltose where the resulting media containing all components of the composition—i.e. said microorganism according to the present invention—can be added as an ingredient to yoghurt milk in suitable concentrations—such as for example in concentrations in the final product which offer a daily dose of $10^6$-$10^{10}$ cfu. The microorganism according to the present invention may be used before or after fermentation of the yoghurt.

Advantageously, where the product is a food product, the probiotic bacteria should remain effective through the normal "sell-by" or "expiration" date during which the food product is offered for sale by the retailer. The effective time may usefully extend past such dates until the end of the normal freshness period when food spoilage becomes apparent. The desired lengths of time and normal shelf life will vary from foodstuff to foodstuff and those of ordinary skill in the art will recognise that shelf-life times will vary upon the type of foodstuff, the size of the foodstuff, storage temperatures, processing conditions, packaging material and packaging equipment.

The bacterial composition of the present invention may be used as, or may be added to, a functional food. As used herein, the term "functional food" means food which is capable of providing not only a nutritional effect and/or a taste, but is also capable of delivering a further beneficial effect to consumer, such as an additional health benefit.

Accordingly, functional foods are ordinary foods that have components or ingredients (such as those described herein) incorporated into them that impart to the food a specific functional benefit, such as a medical or physiological benefit, other than a purely nutritional effect. Although there is no legal definition of a functional food, they are generally foods marketed as having specific health effects.

Some functional foods are nutraceuticals. As used herein, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

According to a further aspect, the present invention relates to the use of a bacterium or metabolite thereof which is demonstrates binding to at least one ABO blood type antigen, or a probiotic composition comprising one or more such bacteria, for the prevention and/or treatment of gastrointestinal disorders.

As used herein, the term "gastrointestinal disorder" includes any disease or disorder relating to the gastrointestinal tract. The disorder may, for example, be one that is known to be associated with an altered composition and diversity of the GIT microbiota. The gastrointestinal disorder may be inflammatory bowel disease (IBD), irritable bowel syndrome (IBS), Crohn's disease, ulcerative colitis, constipation or diarrhoea.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

A pharmaceutically acceptable support may be for example a support in the form of compressed tablets, tablets, capsules, ointments, suppositories or drinkable solutions. Other suitable forms are provided below.

The pharmaceutical may be in the form of a solution or as a solid—depending on the use and/or the mode of application and/or the mode of administration.

The bacterium or metabolite thereof or probiotic composition may be used according to the present invention in any suitable form—whether when alone or when present in a combination with other components or ingredients. The bacteria used in the present invention may be referred to herein as "the composition". Likewise, combinations comprising the composition of the present invention and other components and/or ingredients (i.e. ingredients—such as food ingredients, functional food ingredients or pharmaceutical ingredients) may be used in any suitable form.

The bacterium or metabolite thereof or probiotic composition may be used according to the present invention in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (such as corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like.

Suitable excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules, fibre capsules, fibre tablets or fibre beverages.

It will be apparent to the skilled person that the formulation should ideally be able to remain stable during transit though the gastrointestinal tract; for example, it may be resistant to proteolytic degradation, stable at acid pH and resistant to the detergent effects of bile.

The invention further provides the following disclosure, presented in the form of numbered paragraphs:

1. A bacterium or metabolite thereof characterised by:
   a) an average A antigen adhesion of more than 100% when compared to *L. crispatus* LMG18199; and/or
   a) an average B antigen adhesion of more than 100% when compared to *L. crispatus* LMG18199; and/or
   b) an average O antigen adhesion of more than 100% when compared to *L. crispatus* LMG18199.
2. A bacterium or metabolite thereof according to paragraph 1 wherein said bacterium or metabolite thereof is further characterised by:
   c) more than −2.6 average acid tolerance represented as a log change when measured at pH 2.5 for 1.5 hours as defined in an acid resistance assay; and/or
   d) more than 40% average bile tolerance represented as growth in 0.9% dehydrated fresh bile as a percentage of growth in MRS without bile as defined in a bile resistance assay.
3. A bacterium according to paragraph 1 or 2 wherein said bacterium is deposited as DSM 32111, DSM 32108, DSM 32107, DSM 32098, DSM 32104, DSM 32112, DSM 32109, DSM 32105, DSM 32110, DSM 32103, DSM 32099, DSM 32106, DSM 32097, DSM 32114, DSM 32115 or a mutant, variant and/or progeny thereof.
4. A probiotic composition comprising a bacterium or metabolite thereof according to any one of paragraphs 1 to 3.
5. A probiotic composition according to paragraph 4 further comprising a suitable carrier.
6. A probiotic composition according to any one of paragraphs 4 or 5, which comprises a combination of 2, 3, 4, 5 or 6 bacterial strains or metabolites thereof as defined in any one of claims 1 to 3, optionally in combination with one or more further bacterial strains.
7. A probiotic composition according to any one of paragraphs 4 to 6, wherein the composition further comprises one or more further bacterial strains.
8. A probiotic composition according to paragraph 7, wherein said one or more further bacterial strains are selected from: *Lactobacillus acidophilus* NCFM; *Bifidobacterium lactis* BL-04; *Lactobacillus paracasei* LPC37; *Bifidobacterium lactis* HN019, and/or *Bifidobacterium lactis* Bi-07.
9. A probiotic composition according to paragraph 8 comprising DAVE034, *Lactobacillus acidophilus* NCFM; *Bifidobacterium lactis* BL-04; *Lactobacillus paracasei* LPC37; *Bifidobacterium lactis* HN019 and *Bifidobacterium lactis* Bi-07.
10. A probiotic composition according to any one of the paragraphs 4 to 9, wherein the composition is personalised for an A, B, AB or O blood group individual by comprising one or more bacteria which demonstrate antigen adhesion of more than 100% when compared to *L. crispatus* LMG18199 for the appropriate blood group antigen(s).
11. A probiotic composition according to any one of paragraphs 4 to 10, which further comprises at least one prebiotic component.
12. A method of producing a probiotic composition according to any one of paragraphs 4 to 11, the method comprising combining the selected bacterium or metabolite thereof with a suitable carrier.
13. A food product, dietary supplement, medical food, neutraceutical or pharmaceutical composition comprising a probiotic composition according to any one of paragraphs 4 to 11.
14. A method of selecting a bacterium or metabolite thereof comprising:
    a) admixing one or more test bacteria with an A antigen, B antigen, O antigen or combinations thereof;
    b) admixing one or more *Lactobacillus reuteri* RC-14 control bacteria with A antigen, B antigen, O antigen or combinations thereof;
    c) incubating said admixtures of step a) and b);
    d) comparing the affinity of adhesion to said A antigen, B antigen, O antigen or combinations thereof of the test bacteria and *Lactobacillus reuteri* RC-14; and
    e) selecting bacteria having a higher affinity of adhesion to said A antigen, B antigen, O antigen or combinations thereof than *Lactobacillus reuteri* RC-14.
15. A method according to paragraph 14 wherein said admixtures are incubated in separate vials in step (b).
16. A method according to paragraph 14 or 15, wherein the method is a fluorescence based method.
17. A method according to paragraph 16, wherein bacteria are selected which have:
    i) an average A antigen adhesion intensity of fluorescence of more than 549;
    ii) an average B antigen adhesion intensity of fluorescence of more than 519; and/or
    iii) an average O antigen adhesion intensity of fluorescence of more than 746.
18. A method according to any one of paragraphs 14 to 17 wherein said method further comprises:
    f) assaying the average acid tolerance of the bacteria selected in step e) at pH 2.5 for 1.5 hours; and/or
    g) assaying the average bile tolerance of the bacteria selected in step e) in 0.9% bile; and
    h) selecting one or more bacteria having more than −2.56 average acid tolerance represented as a log change when measured at pH 2.5 for 1.5 hours and/or more than 40.16% average bile tolerance represented as growth in 0.9% bile as a percentage of growth in MRS without bile.

19. A bacterium or metabolite thereof selected by the method of any one of paragraphs 14 to 18.

20. A bacterium according to paragraph 19 wherein said bacterium is deposited as DSM 32111, DSM 32108, DSM 32107, DSM 32098, DSM 32104, DSM 32112, DSM 32109, DSM 32105, DSM 32110, DSM 32103, DSM 32099, DSM 32106, DSM 32097, DSM 32114, DSM 32115 or a mutant, variant and/or progeny thereof.

21. A probiotic composition comprising a bacterium or metabolite thereof according to any one of paragraphs 19 to 20.

22. A probiotic composition according to paragraph 21 further comprising a suitable carrier.

23. A probiotic composition according to any one of paragraphs 21 or 22, which comprises a combination of 2, 3, 4, 5 or 6 bacterial strains or metabolites thereof as defined in any one of the paragraphs 19 to 20, optionally in combination with one or more further bacterial strains.

24. A probiotic composition according to any of paragraphs 21 to 23, wherein the composition further comprises one or more further bacterial strains.

25. A probiotic composition according to paragraph 24, wherein said one or more further bacterial strains are selected from: *Lactobacillus acidophilus* NCFM; *Bifidobacterium lactis* BL-04; *Lactobacillus paracasei* LPC37; *Bifidobacterium lactis* HN019, and/or *Bifidobacterium lactis* Bi-07.

26. A food product, dietary supplement, medical food, neutraceutical or pharmaceutical composition comprising a probiotic composition according to any one of paragraphs 21 to 25.

27. Use of a bacterium or metabolite according to any one of paragraphs 1-3 or 19-20 or selected by the method of any one of paragraphs 14-18, or a probiotic composition according to any one of paragraphs 4-11 or 21-25, for the manufacture of a formulation for preventing and/or treating gastrointestinal disorders.

28. A bacterium or metabolite according to any one of paragraphs 1-3 or 19-20 or selected by the method of any one of paragraphs 14-18, or a probiotic composition according to any one of paragraphs 4-11 or 21-25, for use in preventing and/or treating gastrointestinal disorders.

29. A method of preventing and/or treating gastrointestinal disorders comprising administering to a subject a bacterium or metabolite thereof according to any one of paragraphs 1-3 or 19-20 or selected by the method of any one of paragraphs 14-18, or a probiotic composition according to any one of paragraphs 4-11 or 21-25, in a pharmaceutically effective amount.

30. A method of personalising a probiotic composition or food product for an individual with an A, B, AB or O blood group by selecting for inclusion in the probiotic composition or food product one or more bacteria which demonstrate antigen adhesion of more than 100% when compared to *Lactobacillus reuteri* RC-14 or *L. crispatus* LMG18199 for the appropriate blood group antigen(s).

31. A bacterium, metabolite, probiotic composition, food product, method, bacterium or metabolite for use, use or combinations thereof substantially as described herein with reference to the drawings.

The invention will now be described, by way of example only, with reference to the following Examples.

EXAMPLES

Materials & Methods

Probiotic Properties of the Strains

Acid tolerance of the strains was tested in pH 2.5 and pH 3.5 for 1.5 h and bile tolerance in 0.9% and 0.3% Oxgall (Difco) bile concentrations for 24 h (Saarela et al. 2009). Briefly, the strains were cultivated in duplicate in MRS broth in anaerobic conditions at 37° C. for 18 h. The pelleted cells were washed twice with 10 ml PBS pH 7.2 and resuspended in 0.01 mol/L PBS pH 7.2 so that the optical density ($OD_{600}$) of the sample was 1 (equals to $1 \times 10^8$ CFU/ml). Acid tolerance was tested by incubating cells in PBS pH 7.2. PBS pH 2.5 and PBS pH 3.5 for 90 min at 37° C. The ten-fold dilution series were grown on MRS agar, and colonies were counted after 48 h incubation in anaerobic conditions at 37° C. The results for acid tolerance were expressed as growth log reduction of CFU after exposure to pH 2.5 or 3.5 in comparison to pH 7.2. Bile tolerance was tested by incubating 1:10 diluted strain cultures in MRS containing 0.9% Oxgall, MRS containing 0.3% Oxgall and in plain MRS at 37° C. for 24 in anaerobic conditions. The growth was measured before and after incubation as $OD_{595}$ by Multiskan RC (Labsystems). The bile tolerance results were expressed as % growth (OD) in MRS with 0.9% or 0.3% Oxgall in comparison to growth (OD) in MRS without bile. Additionally, acid and bile tolerance of the strains was compared with that of *Lactobacillus rhamnosus* LGG (VTT E-96666) strain. All the measurements were performed in duplicates and repeated twice for most of the strains.

ABH Antigen Adhesion

The ABH adhesion capability was tested for all strains (H antigen corresponding to blood group O phenotype). The tested blood group antigens A, B and H (Elicityl) were suspended in PBS pH7.2 and biotinylated. The stains were cultivated in anaerobic conditions in MRS plates at 37° C. for 48-72 h. A single colony was re-inoculated to 10 ml MRS broth and cultivated overnight in anaerobic conditions at 37° C. The cells were washed twice with 10 ml PBS pH 7.2 and resuspended in PBS pH 7.2, so that the OD (600 nm) of the sample was set to 1 (equals to $1 \times 10^8$ cfu/ml). The 1 ml sample and 1 ml 10 µg/ml biotinylated antigen solution were mixed together and incubated in slow shaking for 30 min at room temperature, and 100 µl of the mixture transferred in to the Delfia Streptavidin coated 96-well plates (Wallac), which were washed twice with 200 µl PBS pH7.2, followed by wash with SuperBlock (Pierce) three times (2×200 µl+1× 100 µl) and once with 200 µl sterile water. For streptavidin-biotin interaction, the plates were incubated for 30 min at room temperature on slow agitation before washing of the well three times with 200 µl sterile water. Between the washes the plate was incubated for 5 min. To detect the attached bacteria, 200 µl Syto9 dye (diluted 1:6) (Invitrogen) was added to the well and incubated for 15 min in dark. The intensity of Syto-9 stain in well was measured with Wallac Viktor² 1420 multilabel counter (Perkin Elmer). All the measurements were done in four replicates and the results were repeated at least twice. The adhesion of the strains was compared to *Lactobacillus reuteri* RC-14 (available from Christian Hansen A/S, Denmark).

Example 1

A number of different criteria were used to select bacteria of the invention that would have advantageous properties for the production of a probiotic composition.

The criteria used and the cut-off values selected are indicated below in Table 2.

TABLE 2

| Selected criteria: | Control strain | Cut-off value | Results |
|---|---|---|---|
| Acid pH 2.5 | L. Rhamnosus LGG | −2.56 | Average acid tolerance, log change in pH 2.5 for 1.5 h |
| Bile 0.9% | L. Rhamnosus LGG | 40.16% | Average bile tolerance, growth in 0.9% oxgall as % of growth in MRS w/o bile |
| A antigen adhesion | L. crispatus LMG18199 | 100% | Average A antigen adhesion, intensity of fluorescence |
| B antigen adhesion | L. crispatus LMG18199 | 100% | Average B antigen adhesion, intensity of fluorescence |
| O antigen adhesion | L. crispatus LMG18199 | 100% | Average O antigen adhesion, intensity of fluorescence |

The assays were carried out as indicated above in the Materials and Methods section. The results of these analyses are presented below for a number of strains, including the control strains *L. rhamnosus* LGG, RC-14, GR-1 and *L. crispatus* LMG18199.

TABLE 3

Results of the acid tolerance studies at pH2.5 for 1.5 hours.

| Deposit number(s) | DGCC strain number | Other strain code/ commercial ID | Identification | Acid tolerance log change in pH 2.5 for 1.5 h | Acid tolerance log change in pH 2.5 for 1.5 h | Average acid tolerance, log change in pH 2.5 for 1.5 h |
|---|---|---|---|---|---|---|
| DSM 32107 | 11860 | LX11860 | L. brevis | −5.2 | | −5.2 |
| DSM 32363 | 4022 | LA0893 | L. acidophilus | −5.7 | −4.3 | −5.0 |
| PTA-4800 | 9868 | LS-33 | L. salivarius | −4.6 | −4.8 | −4.7 |
| DSM 32109 | 11865 | LX11865 | L. fermentum | −4.3 | −5.1 | −4.7 |
| DSM 32112 | 11853 | LX11853 | L. fermentum | −5.3 | −3.6 | −4.5 |
| DSM 32110 | 11866 | LX11866 | L. fermentum | −4.5 | | −4.5 |
| DSM 32108 | 11864 | LX11864 | L. brevis | −5.4 | −3.5 | −4.5 |
| SD 5584 | 8656 | M61/Ll-23 | Lactococcus lactis Ll-23 | −4.3 | −4.1 | −4.2 |
| SD 5214 | 9912 | LBr-35 | L. brevis | −4.1 | −3.2 | −3.7 |
| DSM32099 | 11854 | LX11854 | L. mucosae | −3.2 | −3.5 | −3.4 |
| DSM32105 | 1925 | 1925 | L. fermentum | −4.0 | −2.5 | −3.2 |
| SD5209, PTA-4799, DSM 22266 | 4715 | LP0115 | L. plantarum | −3.1 | −2.9 | −3.0 |
| SD 5589 | 4106 | LB0064 | L. delbrueckii bulgaricus | −3.2 | −2.4 | −2.8 |
| SD 5212 | 9353 | La-11/La-14 | L. acidophilus | −4.2 | −1.2 | −2.7 |
| | | | L. Rhamnosus LGG | | | −2.6 |
| DSM32111 | 11884 | LA11884 | L. acidophilus | −1.8 | −3.2 | −2.5 |
| DSM32114 | 11862 | LX11862 | L. rhamnosus | −3.3 | −1.8 | −2.5 |
| PTA-4798 | 4981 | LQ0281/LPC-37 | L. paracasei | −2.6 | −2.5 | −2.5 |
| DSM32098 | 11873 | LX11873 | L. acidophilus | −2.3 | −2.2 | −2.3 |
| DSM 22193, SD 5217 | 9913 | Lr-32 | L. rhamnosus | −2.1 | −2.4 | −2.2 |
| DSM22091, SD5221, PTA-4797 | 8698 | NCFM | L. acidophilus | −1.3 | −3.2 | −2.2 |
| DSM 22876, SD 5675 | 1460 | 1460/HN001 | L. rhamnosus | −2.2 | −2.2 | −2.2 |
| DSM 32115 | 11881 | LX11881 | L. rhamnosus | −1.5 | −2.6 | −2.0 |
| DSM 32097 | 11887 | LX11887 | L. paracasei | −1.1 | −1.6 | −1.3 |
| DSM 32103 | 5111 | LG0179 | L. gasseri | −0.6 | −1.2 | −0.9 |
| SD 5585 | 10687 | LG10687/LG-36 | L. gasseri | 0.1 | −0.1 | 0.0 |

TABLE 4

Results of the acid tolerance studies at pH3.5 for 1.5 hours

| Deposit number(s) | DGCC strain number | Other strain code/ commercial ID | Identification | Acid tolerance, log change in pH 3.5 for 1.5 h | Acid tolerance, log change in pH 3.5 for 1.5 h | Average acid tolerance, log change in pH 3.5 for 1.5 h |
|---|---|---|---|---|---|---|
| DSM22091, SD5221, PTA-4797 | 8698 | NCFM | L. acidophilus | −0.1 | −0.1 | −0.1 |
| DSM 32363 | 4022 | LA0893 | L. acidophilus | 0.0 | 0.3 | 0.1 |
| SD 5212 | 9353 | La-11/La-14 | L. acidophilus | −0.4 | 0.0 | −0.2 |
| SD 5214 | 9912 | LBr-35 | L. brevis | −0.5 | 0.1 | −0.2 |
| SD 5213 | 9864 | Lc-11 | L. casei | −0.1 | −0.1 | −0.1 |
| SD 5589 | 4106 | LB0064 | L. delbrueckii bulgaricus | −0.1 | 0.0 | −0.1 |
| DSM 32104 | 11852 | LX11852 | L. fermentum | −0.2 | | −0.2 |
| DSM 32112 | 11853 | LX11853 | L. fermentum | −0.1 | | −0.1 |
| DSM 32109 | 11865 | LX11865 | L. fermentum | −0.3 | | −0.3 |
| DSM 32110 | 11866 | LX11866 | L. fermentum | −0.3 | | −0.3 |
| SD 5585 | 10687 | LG10687/LG-36 | L. gasseri | 0.0 | 0.1 | 0.1 |
| PTA-4798 | 4981 | LQ0281/LPC-37 | L. paracasei | −0.1 | | −0.1 |
| SD5209, PTA-4799, DSM 22266 | 4715 | LP0115 | L. plantarum | −0.1 | −0.1 | −0.1 |
| DSM 32106 | 11858 | LX11858 | L. paracasei | −0.1 | | −0.1 |
| DSM 22876, SD 5675 | 1460 | 1460/HN001 | L. rhamnosus | 0.0 | 0.0 | 0.0 |
| DSM 22193, SD 5217 | 9913 | Lr-32 | L. rhamnosus | −0.1 | 0.0 | −0.1 |
| PTA-4800 | 9868 | LS-33 | L. salivarius | 0.0 | 0.1 | 0.0 |
| SD 5584 | 8656 | M61/Ll-23 | Lactococcus lactis Ll-23 | −0.2 | −0.2 | −0.2 |
| DSM 32111 | 11884 | LA11884 | L. acidophilus | −0.2 | | −0.2 |
| DSM 32108 | 11864 | LX11864 | L. brevis | −0.2 | | −0.2 |
| DSM 32107 | 11860 | LX11860 | L. brevis | −0.5 | | −0.5 |
| DSM 32098 | 11873 | LX11873 | L. acidophilus | 0.0 | | 0.0 |
| DSM 32105 | 1925 | 1925 | L. fermentum | 0.1 | 0.2 | 0.2 |
| DSM 32103 | 5111 | LG0179 | L. gasseri | −0.3 | 0.1 | −0.1 |
| DSM 32099 | 11854 | LX11854 | L. mucosae | 0.0 | −0.4 | −0.2 |
| DSM 32097 | 11887 | LX11887 | L. paracasei | 0.0 | | 0.0 |
| DSM 32114 | 11862 | LX11862 | L. rhamnosus | −0.1 | | −0.1 |
| DSM 32115 | 11881 | LX11881 | L. rhamnosus | 0.7 | | 0.7 |
| | | | L. Rhamnosus LGG | | | −0.1 |

TABLE 5

Results of the bile tolerance studies in 0.9% oxgall as % of growth in MRS without bile.

| Deposit number(s) | DGCC strain number | Other strain code/commercial ID | Identification | Bile tolerance, growth in 0.9% oxgall as % of growth in MRS w/o bile | | | Average bile tolerance, growth in 0.9% oxgall as % of growth in MRS w/o bile |
|---|---|---|---|---|---|---|---|
| SD 5589 | 4106 | LB0064 | L. delbrueckii bulgaricus | 5% | 2% | | 3% |
| DSM 32363 | 4022 | LA0893 | L. acidophilus | 9% | 5% | 2% | 5% |
| SD 5584 | 8656 | M61/Ll-23 | Lactococcus lactis Ll-23 | 1% | 11% | | 6% |
| DSM 32103 | 5111 | LG0179 | L. gasseri | 19% | 5% | | 12% |
| SD 5585 | 10687 | LG10687/LG-36 | L. gasseri | 15% | 16% | | 15% |
| SD 5213 | 9864 | Lc-11 | L. casei | 17% | 15% | | 16% |
| PTA-4800 | 9868 | LS-33 | L. salivarius | 23% | 21% | | 22% |
| PTA-4798 | 4981 | LQ0281/LPC-37 | L. paracasei | 22% | 23% | | 22% |
| DSM 22876, SD 5675 | 1460 | 1460/HN001 | L. rhamnosus | 29% | 35% | | 32% |

TABLE 5-continued

Results of the bile tolerance studies in 0.9% oxgall as % of growth in MRS without bile.

| Deposit number(s) | DGCC strain number | Other strain code/commercial ID | Identification | Bile tolerance, growth in 0.9% oxgall as % of growth in MRS w/o bile | | | Average bile tolerance, growth in 0.9% oxgall as % of growth in MRS w/o bile |
|---|---|---|---|---|---|---|---|
| DSM 32097 | 11887 | LX11887 | L. paracasei | 29% | 40% | | 35% |
| DSM 32106 | 11858 | LX11858 | L. paracasei | 36% | | | 36% |
| DSM 22193, SD 5217 | 9913 | Lr-32 | L. rhamnosus | 36% | 35% | | 36% |
| DSM 32114 | 11862 | LX11862 | L. rhamnosus | 27% | 44% | | 36% |
| DSM 32115 | 11881 | LX11881 | L. rhamnosus | 44% | 34% | | 39% |
| | | | L. Rhamnosus LGG | | | | 40% |
| DSM 32107 | 11860 | LX11860 | L. brevis | 42% | | | 42% |
| DSM 32109 | 11865 | LX11865 | L. fermentum | 34% | 51% | | 43% |
| DSM 32105 | 1925 | 1925 | L. fermentum | 55% | 50% | 35% | 46% |
| DSM 32112 | 11853 | LX11853 | L. fermentum | 43% | 50% | | 47% |
| DSM 32104 | 11852 | LX11852 | L. fermentum | 46% | 50% | | 48% |
| DSM 32108 | 11864 | LX11864 | L. brevis | 47% | 65% | | 56% |
| SD 5214 | 9912 | LBr-35 | L. brevis | 71% | 77% | | 74% |
| DSM 32111 | 11884 | LA11884 | L. acidophilus | 104% | 110% | | 107% |
| SD 5212 | 9353 | La-11/La-14 | L. acidophilus | 113% | 106% | 113% | 111% |
| DSM22091, SD5221, PTA-4797 | 8698 | NCFM | L. acidophilus | 115% | 111% | 116% | 114% |
| DSM 32098 | 11873 | LX11873 | L. acidophilus | 120% | 119% | | 119% |
| DSM 32099 | 11854 | LX11854 | L. mucosae | 142% | 163% | | 152% |

TABLE 6

Results of the bile tolerance studies in 0.3% oxgall as % of growth in MRS without bile.

| Deposit number(s) | DGCC strain number | Other strain code/ commercial ID | Identification | Bile tolerance, growth in 0.3% oxgall as % of growth in MRS w/o bile | | | Average bile tolerance, growth in 0.3% oxgall as % of growth in MRS w/o bile |
|---|---|---|---|---|---|---|---|
| DSM22091, SD5221, PTA-4797 | 8698 | NCFM | L. acidophilus | 93% | 91% | 85% | 90% |
| DSM 32363 | 4022 | LA0893 | L. acidophilus | 2% | 3% | 2% | 2% |
| SD 5212 | 9353 | La-11/La-14 | L. acidophilus | 92% | 89% | 85% | 88% |
| SD 5214 | 9912 | LBr-35 | L. brevis | 92% | 93% | | 92% |
| SD 5213 | 9864 | Lc-11 | L. casei | 30% | 31% | | 30% |
| SD 5589 | 4106 | LB0064 | L. delbrueckii bulgaricus | 9% | 5% | | 7% |
| DSM 32104 | 11852 | LX11852 | L. fermentum | 64% | | | 64% |
| DSM 32112 | 11853 | LX11853 | L. fermentum | 64% | | | 64% |
| DSM 32109 | 11865 | LX11865 | L. fermentum | 64% | 63% | | 63% |
| DSM 32110 | 11866 | LX11866 | L. fermentum | 21% | | | 21% |
| SD 5585 | 10687 | LG10687/LG-36 | L. gasseri | 33% | 39% | | 36% |
| PTA-4798 | 4981 | LQ0281/LPC-37 | L. paracasei | 46% | 43% | | 45% |
| SD5209, PTA-4799, DSM 22266 | 4715 | LP0115 | L. plantarum | 85% | 90% | | 88% |
| DSM 32106 | 11858 | LX11858 | L. paracasei | 55% | | | 55% |
| DSM 22876, SD 5675 | 1460 | 1460/HN001 | L. rhamnosus | 62% | 63% | | 63% |
| DSM 22193, SD 5217 | 9913 | Lr-32 | L. rhamnosus | 70% | 66% | | 68% |
| PTA-4800 | 9868 | LS-33 | L. salivarius | 73% | 68% | | 71% |
| SD 5584 | 8656 | M61/Ll-23 | Lactococcus lactis Ll-23 | 2% | 8% | | 5% |
| DSM 32111 | 11884 | LA11884 | L. acidophilus | 89% | 85% | | 87% |
| DSM 32108 | 11864 | LX11864 | L. brevis | 76% | 63% | | 70% |

TABLE 6-continued

Results of the bile tolerance studies in 0.3% oxgall as % of growth in MRS without bile.

| Deposit number(s) | DGCC strain number | Other strain code/ commercial ID | Identification | Bile tolerance, growth in 0.3% oxgall as % of growth in MRS w/o bile | | | Average bile tolerance, growth in 0.3% oxgall as % of growth in MRS w/o bile |
|---|---|---|---|---|---|---|---|
| DSM 32107 | 11860 | LX11860 | L. brevis | 72% | | | 72% |
| DSM 32098 | 11873 | LX11873 | L. acidophilus | 99% | 98% | | 99% |
| DSM 32105 | 1925 | 1925 | L. fermentum | 83% | 77% | 76% | 79% |
| DSM 32103 | 5111 | LG0179 | L. gasseri | 60% | 47% | | 53% |
| DSM 32099 | 11854 | LX11854 | L. mucosae | 167% | | | 167% |
| DSM 32097 | 11887 | LX11887 | L. paracasei | 39% | 68% | | 54% |
| DSM 32114 | 11862 | LX11862 | L. rhamnosus | 61% | 60% | | 60% |
| DSM 32115 | 11881 | LX11881 | L. rhamnosus | 58% | 58% | | 58% |
| | | | L. Rhamnosus LGG | | | | 62.66% |

TABLE 7

Growth in MRS as a control for Tables 5 and 6 above.

| Deposit number(s) | DGCC strain number | Other strain code/ commercial ID | Identification | Growth in MRS, OD (A600) | | | Average growth in MRS, OD (A600) |
|---|---|---|---|---|---|---|---|
| DSM22091, SD5221, PTA-4797 | 8698 | NCFM | L. acidophilus | 1.1 | 1.1 | 1.1 | 1.1 |
| DSM 32363 | 4022 | LA0893 | L. acidophilus | 1.2 | 1.1 | 1.2 | 1.2 |
| SD 5212 | 9353 | La-11/La-14 | L. acidophilus | 1.1 | 1.1 | 1.1 | 1.1 |
| SD 5214 | 9912 | LBr-35 | L. brevis | 0.9 | 1.0 | | 1.0 |
| SD 5213 | 9864 | Lc-11 | L. casei | 1.2 | 1.2 | | 1.2 |
| SD 5589 | 4106 | LB0064 | L. delbrueckii bulgaricus | 1.1 | 1.1 | | 1.1 |
| DSM 32104 | 11852 | LX11852 | L. fermentum | 1.0 | 0.9 | | 0.9 |
| DSM 32112 | 11853 | LX11853 | L. fermentum | 1.0 | 0.9 | | 0.9 |
| DSM 32109 | 11865 | LX11865 | L. fermentum | 1.0 | 0.9 | | 0.9 |
| DSM 32110 | 11866 | LX11866 | L. fermentum | 0.8 | | | 0.8 |
| SD 5585 | 10687 | LG10687/LG-36 | L. gasseri | 1.0 | 1.0 | | 1.0 |
| PTA-4798 | 4981 | LQ0281/LPC-37 | L. paracasei | 1.2 | 1.1 | | 1.1 |
| SD5209, PTA-4799, DSM 22266 | 4715 | LP0115 | L. plantarum | 1.2 | 1.2 | | 1.2 |
| DSM 32106 | 11858 | LX11858 | L. paracasei | 1.2 | | | 1.2 |
| DSM 22876, SD 5675 | 1460 | 1460/HN001 | L. rhamnosus | 1.2 | 1.2 | | 1.2 |
| DSM 22193, SD 5217 | 9913 | Lr-32 | L. rhamnosus | 1.2 | 1.2 | | 1.2 |
| PTA-4800 | 9868 | LS-33 | L. salivarius | 1.3 | 1.3 | | 1.3 |
| SD 5584 | 8656 | M61/Ll-23 | Lactococcus lactis Ll-23 | 1.0 | 1.1 | | 1.1 |
| DSM 32111 | 11884 | LA11884 | L. acidophilus | 1.1 | 1.1 | | 1.1 |
| DSM 32108 | 11864 | LX11864 | L. brevis | 0.9 | 1.1 | | 1.0 |
| DSM 32107 | 11860 | LX11860 | L. brevis | 0.9 | | | 0.9 |
| DSM 32098 | 11873 | LX11873 | L. acidophilus | 1.0 | 1.0 | | 1.0 |
| DSM 32105 | 1925 | 1925 | L. fermentum | 1.1 | 1.0 | 1.0 | 1.1 |
| DSM 32103 | 5111 | LG0179 | L. gasseri | 1.1 | 1.0 | | 1.0 |
| DSM 32099 | 11854 | LX11854 | L. mucosae | 0.8 | 0.5 | | 0.6 |
| DSM 32097 | 11887 | LX11887 | L. paracasei | 1.0 | 1.0 | | 1.0 |
| DSM 32114 | 11862 | LX11862 | L. rhamnosus | 1.2 | 1.2 | | 1.2 |
| DSM 32115 | 11881 | LX11881 | L. rhamnosus | 1.1 | 1.2 | | 1.2 |
| | | | L. Rhamnosus LGG | | | | 1.1 |

TABLE 8

Results from the A antigen adhesion studies.

| Deposit number(s) | DGCC strain number | Other strain code/ commercial ID | Identification | A antigen adhesion, % of adhesion of L. crispatus LMG 18199 | | | | | | Average A antigen adhesion, % of adhesion of L. crispatus LMG 18199 |
|---|---|---|---|---|---|---|---|---|---|---|
| DSM22091, SD5221, PTA-4797 | 8698 | NCFM | L. acidophilus | 0% | 5% | | | | | 2% |
| DSM 32363 | 4022 | LA0893 | L. acidophilus | 2% | 3% | | | | | 3% |
| SD 5212 | 9353 | La-11/La-14 | L. acidophilus | 0% | 2% | | | | | 1% |
| SD 5214 | 9912 | LBr-35 | L. brevis | 0% | 1% | | | | | 1% |
| SD 5213 | 9864 | Lc-11 | L. casei | −2% | −1% | | | | | −1% |
| SD 5589 | 4106 | LB0064 | L. delbrueckii bulgaricus | −1% | 0% | | | | | 0% |
| DSM 32104 | 11852 | LX11852 | L. fermentum | 133% | 188% | 112% | | | | 144% |
| DSM 32112 | 11853 | LX11853 | L. fermentum | 144% | 151% | 137% | 122% | 126% | 222% | 150% |
| DSM 32109 | 11865 | LX11865 | L. fermentum | 116% | 91% | 120% | 104% | 137% | 201% | 128% |
| DSM 32110 | 11866 | LX11866 | L. fermentum | 102% | 135% | 105% | 106% | | | 112% |
| SD 5585 | 10687 | LG10687/LG-36 | L. gasseri | −1% | 0% | | | | | 0% |
| PTA-4798 | 4981 | LQ0281/LPC-37 | L. paracasei | 0% | 1% | | | | | 1% |
| SD5209, PTA-4799, DSM 22266 | 4715 | LP0115 | L. plantarum | 0% | 0% | | | | | 0% |
| DSM 32106 | 11858 | LX11858 | L. paracasei | 73% | 169% | | | | | 121% |
| DSM 22876, SD 5675 | 1460 | 1460/HN001 | L. rhamnosus | 46% | | | | | | 46% |
| DSM 22193, SD 5217 | 9913 | Lr-32 | L. rhamnosus | −2% | 59% | | | | | 28% |
| PTA-4800 | 9868 | LS-33 | L. salivarius | 0% | 2% | | | | | 1% |
| SD 5584 | 8656 | M61/Ll-23 | Lactococcus lactis Ll-23 | 1% | 3% | | | | | 2% |
| DSM 32111 | 11884 | LA11884 | L. acidophilus | 0% | 5% | 111% | | | | 39% |
| DSM 32108 | 11864 | LX11864 | L. brevis | 31% | 47% | 57% | | | | 45% |
| DSM 32107 | 11860 | LX11860 | L. brevis | −1% | 37% | | | | | 18% |
| DSM 32098 | 11873 | LX11873 | L. acidophilus | 30% | | | | | | 30% |
| DSM 32105 | 1925 | 1925 | L. fermentum | −1% | 0% | | | | | 0% |
| DSM 32103 | 5111 | LG0179 | L. gasseri | −1% | 5% | | | | | 2% |
| DSM 32099 | 11854 | LX11854 | L. mucosae | 4% | 17% | | | | | 11% |
| DSM 32097 | 11887 | LX11887 | L. paracasei | 0% | 3% | 3% | 172% | | | 45% |
| DSM 32114 | 11862 | LX11862 | L. rhamnosus | 0% | 1% | 24% | 36% | 88% | | 30% |
| DSM 32115 | 11881 | LX11881 | L. rhamnosus | 55% | | | | | | 55% |
| | | | L. crispatus LMG18199 | | | | | | | 100% |

TABLE 9

Results from the B antigen adhesion studies.

| Deposit number(s) | DGCC strain number | Other strain code/commercial ID | Identification | B antigen adhesion, % of adhesion of L. crispatus LMG 18199 | | | | | Average B antigen adhesion, % of adhesion of L. crispatus LMG 18199 |
|---|---|---|---|---|---|---|---|---|---|
| DSM22091, SD5221, PTA-4797 | 8698 | NCFM | L. acidophilus | 0% | 4% | | | | 2% |
| DSM 32363 | 4022 | LA0893 | L. acidophilus | 1% | | | | | 1% |
| SD 5212 | 9353 | La-11/La-14 | L. acidophilus | 0% | 2% | | | | 1% |
| SD 5214 | 9912 | LBr-35 | L. brevis | 1% | 1% | 33% | | | 12% |
| SD 5213 | 9864 | Lc-11 | L. casei | −1% | 1% | | | | 0% |
| SD 5589 | 4106 | LB0064 | L. delbrueckii bulgaricus | −1% | 0% | | | | 0% |
| DSM 32104 | 11852 | LX11852 | L. fermentum | 121% | 109% | 179% | 114% | | 131% |
| DSM 32112 | 11853 | LX11853 | L. fermentum | 132% | 113% | 148% | 203% | 118% | 143% |
| DSM 32109 | 11865 | LX11865 | L. fermentum | 80% | 111% | 113% | 139% | 131% | 117% | 115% |
| DSM 32110 | 11866 | LX11866 | L. fermentum | 127% | 103% | 98% | 100% | | 107% |
| SD 5585 | 10687 | LG10687/LG-36 | L. gasseri | 1% | 1% | | | | 1% |
| PTA-4798 | 4981 | LQ0281/LPC-37 | L. paracasei | 1% | 2% | | | | 2% |
| SD5209, PTA-4799, DSM 22266 | 4715 | LP0115 | L. plantarum | −1% | 1% | | | | 0% |
| DSM 32106 | 11858 | LX11858 | L. paracasei | −1% | 58% | | | | 29% |
| DSM 22876, SD 5675 | 1460 | 1460/HN001 | L. rhamnosus | −1% | 3% | | | | 1% |
| DSM 22193, SD 5217 | 9913 | Lr-32 | L. rhamnosus | 1% | 63% | | | | 32% |

TABLE 9-continued

Results from the B antigen adhesion studies.

| Deposit number(s) | DGCC strain number | Other strain code/commercial ID | Identification | B antigen adhesion, % of adhesion of L. crispatus LMG 18199 | | | | | Average B antigen adhesion, % of adhesion of L. crispatus LMG 18199 |
|---|---|---|---|---|---|---|---|---|---|
| PTA-4800 | 9868 | LS-33 | L. salivarius | 1% | 1% | | | | 1% |
| SD 5584 | 8656 | M61/Ll-23 | Lactococcus lactis Ll-23 | 1% | 2% | | | | 1% |
| DSM 32111 | 11884 | LA11884 | L. acidophilus | 1% | 4% | 18% | | | 8% |
| DSM 32108 | 11864 | LX11864 | L. brevis | 21% | 23% | | | | 22% |
| DSM 32107 | 11860 | LX11860 | L. brevis | 0% | 27% | | | | 14% |
| DSM 32098 | 11873 | LX11873 | L. acidophilus | 30% | | | | | 30% |
| DSM 32105 | 1925 | 1925 | L. fermentum | −1% | 13% | 1% | | | 4% |
| DSM 32103 | 5111 | LG0179 | L. gasseri | 0% | 5% | | | | 3% |
| DSM 32099 | 11854 | LX11854 | L. mucosae | 3% | 14% | | | | 9% |
| DSM 32097 | 11887 | LX11887 | L. paracasei | 4% | 60% | | | | 21% |
| DSM 32114 | 11862 | LX11862 | L. rhamnosus | −1% | 1% | 20% | 18% | 34% | 15% |
| DSM 32115 | 11881 | LX11881 | L. rhamnosus | 50% | | | | | 50% |
| | | | L. crispatus LMG18199 | | | | | | 100% |

TABLE 10

Results from the O antigen adhesion studies.

| Deposit number(s) | DGCC strain number | Other strain code/commercial ID | Identification | O antigen adhesion, % of adhesion of L. crispatus LMG 18199 | | | | | Average O antigen adhesion, % of adhesion of L. crispatus LMG 18199 |
|---|---|---|---|---|---|---|---|---|---|
| DSM22091, SD5221, PTA-4797 | 8698 | NCFM | L. acidophilus | 0% | 4% | | | | 2% |
| DSM 32363 | 4022 | LA0893 | L. acidophilus | 2% | 3% | | | | 3% |
| SD 5212 | 9353 | La-11/La-14 | L. acidophilus | 1% | 2% | | | | 2% |
| SD 5214 | 9912 | LBr-35 | L. brevis | 1% | 2% | | | | 2% |
| SD 5213 | 9864 | Lc-11 | L. casei | −1% | 1% | | | | 0% |
| SD 5589 | 4106 | LB0064 | L. delbrueckii bulgaricus | 0% | 2% | | | | 1% |
| DSM 32104 | 11852 | LX11852 | L. fermentum | 112% | 100% | 176% | 110% | | 124% |
| DSM 32112 | 11853 | LX11853 | L. fermentum | 122% | 106% | 138% | 121% | 269% | 151% |
| DSM 32109 | 11865 | LX11865 | L. fermentum | 77% | 111% | 114% | 99% | 110% 130% | 107% |
| DSM 32110 | 11866 | LX11866 | L. fermentum | 123% | 94% | 101% | 116% | | 108% |
| SD 5585 | 10687 | LG10687/LG-36 | L. gasseri | 1% | 2% | | | | 2% |
| PTA-4798 | 4981 | LQ0281/LPC-37 | L. paracasei | 1% | 2% | | | | 2% |
| SD5209, PTA-4799, DSM 22266 | 4715 | LP0115 | L. plantarum | 0% | 3% | | | | 1% |
| DSM 32106 | 11858 | LX11858 | L. paracasei | 0% | 0% | | | | 0% |
| DSM 22876, SD 5675 | 1460 | 1460/HN001 | L. rhamnosus | 0% | 2% | | | | 1% |
| DSM 22193, SD 5217 | 9913 | Lr-32 | L. rhamnosus | 0% | 1% | | | | 1% |
| PTA-4800 | 9868 | LS-33 | L. salivarius | 1% | 3% | | | | 2% |
| SD 5584 | 8656 | M61/Ll-23 | Lactococcus lactis Ll-23 | 3% | 5% | | | | 4% |
| DSM 32111 | 11884 | LA11884 | L. acidophilus | 0% | 1% | 5% | | | 2% |
| DSM 32108 | 11864 | LX11864 | L. brevis | 16% | 18% | 22% | | | 19% |
| DSM 32107 | 11860 | LX11860 | L. brevis | 1% | 10% | | | | 6% |
| DSM 32098 | 11873 | LX11873 | L. acidophilus | 26% | | | | | 26% |
| DSM 32105 | 1925 | 1925 | L. fermentum | 0% | 1% | | | | 0% |
| DSM 32103 | 5111 | LG0179 | L. gasseri | 1% | 5% | | | | 3% |
| DSM 32099 | 11854 | LX11854 | L. mucosae | 3% | 13% | | | | 8% |
| DSM 32114 | 11862 | LX11862 | L. rhamnosus | 3% | 7% | 20% | 30% | 22% | 16% |
| DSM 32115 | 11881 | LX11881 | L. rhamnosus | 37% | | | | | 37% |
| | | | L. crispatus LMG18199 | | | | | | 100% |

No data was obtained for DSM 32097 in this assay.

No data was obtained for DSM 32097 in this assay.

Based on the data acquired above and the selection criteria used a number of strains were selected according to their suitability for use in a probiotic composition. Table 11 below shows those strains that performed better than control strains based on A, B and O antigen adhesion, and which strains showed enhanced bile and/or acid tolerance. A, B and/or O adhesion of five strains (DSM 32104, DSM 32112, DSM 32109, DSM 32110 and DSM 32106) was equal or better than the adhesion of control strain *L. crispatus* LMG18199, which adheres well to the A antigen (Uchida et al. 2006).

TABLE 11

Strains grouped in accordance with their properties based on criteria as defined in Table 2

| Properties | Strains performing better than control strain(s) | |
|---|---|---|
| A, B and/or O antigen adhesion in vitro | DGCC11852 | DSM 32104 |
| | DGCC11853 | DSM 32112 |
| | DGCC11865 | DSM 32109 |
| | DGCC11866 | DSM 32110 |
| | DGCC11858 | DSM 32106 |
| Acid and/or bile tolerance | DGCC11884 | DSM 32111 |
| | DGCC11864 | DSM 32108 |
| | DGCC11860 | DSM 32107 |
| | DGCC11873 | DSM 32098 |
| | DGCC1925 | DSM 32105 |
| | DGCC5111 | DSM 32103 |
| | DGCC11854 | DSM 32099 |
| | DGCC11887 | DSM 32097 |
| | DGCC11862 | DSM 32114 |
| | DGCC11881 | DSM 32115 |
| A, B and/or O antigen adhesion in vitro + acid and/or bile tolerance | DGCC11852 | DSM 32104 |
| | DGCC11853 | DSM 32112 |

Example 3 (Gastrointestinal Health—Pain)

Male rats weighing approximately 200-220 g are surgically prepared for electromyography of the abdominal muscles in order to measure the pain response to colonic distension later on. Rats are then gavaged with each probiotic (daily dose of $10^7$, $10^8$ and/or $10^9$ CFU) or saline for 7-21 days before a colorectal distension test. Rats are accustomed to polypropylene tunnels 3-5 days before the distension test. The balloon used for distention is taken from an embolectomy probe and is inserted into the rectum at 1 cm from the anus and fixed at the basis of the tail. Increasing levels of distensions are then induced with the probe connected to a barostat. A functional ingredient desensitizes the colonic wall and leads to an increased pain threshold or decreased contraction of the abdominal muscles. Contractions corresponding to each pressure level are measured and compared between groups.

Example 4 (Gastrointestinal Health—Inflammation)

Male rats weighing approximately 200-220 g are gavaged with each probiotic or saline for 15 days before inducing trinitrobenzene sulfonic acid (TNBS) colitis. TNBS is infused intrarectally after an overnight fast at a maximum of 80 mg/kg in 0.3 ml 50% ethanol. Two to four days after TNBS infusion, rats are subjected to the colonic distension test and sacrificed. At sacrifice, tissue specimens, blood and GI contents are collected for further analyses, such as one or more of the following:
Scoring of Inflammation
Fresh tissue specimens are visually scored by an experienced scientist to determine the level of inflammation.
Expression of Inflammation Markers
Sections of colon are snap-frozen in liquid nitrogen. RNA is extracted and converted to cDNA with a commercially available kit. The expression of inflammation markers, such as IL-6, TNF-alpha, IL-1beta, matrix metalloproteinases (MMPs) and their tissue inhibitors, in colonic tissue is analyzed with RT-qPCR.
Colonic Histology
Histological samples are cut from tissues embedded in paraffin, and are visualized under a microscope to enumerate infiltrated immune cells.
Circulating Inflammation Markers
Blood is centrifuged to separate plasma. Inflammation markers (such as IL-6, TNF-alpha, IL-1beta, hsCRP) are then determined with commercially available ELISA kits.
Circulating Lipopolysaccharide
Blood is centrifuged to separate serum. Lipopolysaccharides are analyzed from serum samples using a standard kit based on a Limulus amebocyte extract (the LAL kit), which is commercially available.
Gut Microbiota Analysis
Gut microbiota is analyzed from feces or caecum by extracting DNA. Samples then undergo gut microbial sequencing. Results are analyzed by a trained bioinformatician.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:
1. A method of preventing or treating a gastrointestinal disorder comprising: administering to a subject in need thereof a pharmaceutically effective amount of bacteria, wherein the bacteria comprise *Lactobacillus acidophilus* DSM 32111, *Lactobacillus brevis* DSM 32108, *Lactobacillus brevis* DSM 32107, *Lactobacillus acidophilus* DSM 32098, *Lactobacillus fermentum* DSM 32104, *Lactobacillus fermentum* DSM 32112, *Lactobacillus fermentum* DSM 32109, *Lactobacillus fermentum* DSM 32105, *Lactobacillus fermentum* DSM 32110, *Lactobacillus gasseri* DSM 32103, *Lactobacillus mucosae* DSM 32099, *Lactobacillus paracasei* DSM 32106, *Lactobacillus paracasei* DSM 32097, *Lactobacillus rhamnosus* DSM 32114 and/or *Lactobacillus rhamnosus* DSM 32115.
2. A method of claim 1, wherein the method comprises administering to the subject a pharmaceutically effective amount of *Lactobacillus acidophilus* DSM 32111, *Lactobacillus brevis* DSM 32108, *Lactobacillus brevis* DSM 32107, *Lactobacillus acidophilus* DSM 32098, *Lactobacillus fermentum* DSM 32104, *Lactobacillus fermentum* DSM 32112, *Lactobacillus fermentum* DSM 32109, *Lactobacillus fermentum* DSM 32105, *Lactobacillus fermentum* DSM 32110, *Lactobacillus gasseri* DSM 32103, *Lactobacillus mucosae* DSM 32099, *Lactobacillus paracasei* DSM 32106, *Lactobacillus paracasei* DSM 32097, *Lactobacillus rhamnosus* DSM 32114 or *Lactobacillus rhamnosus* DSM 32115.
3. The method of claim 2, wherein the method further comprises administering to the subject *Lactobacillus acidophilus* NCFM, *Bifidobacterium lactis* BL-04, *Lactobacillus paracasei* LPC37, *Bifidobacterium lactis* HN019 or *Bifidobacterium lactis* Bi-07.

4. The method of claim 3, wherein the method comprises administering to the subject *Lactobacillus fermentum* DSM 32109, *Lactobacillus acidophilus* NCFM, *Bifidobacterium lactis* BL-04, *Lactobacillus paracasei* LPC37, *Bifidobacterium lactis* HN019 and *Bifidobacterium lactis* Bi-07.

5. The method of claim 1, wherein the gastrointestinal disorder comprises inflammatory bowel disease, irritable bowel syndrome, Crohn's disease, ulcerative colitis, constipation or diarrhea.

6. The method of claim 2, wherein the method comprises administering to the subject a pharmaceutically effective amount of DSM 32109.

7. The method of claim 2, wherein the gastrointestinal disorder comprises inflammatory bowel disease, irritable bowel syndrome, Crohn's disease, ulcerative colitis, constipation or diarrhea.

8. The method of claim 3, wherein the gastrointestinal disorder comprises inflammatory bowel disease, irritable bowel syndrome, Crohn's disease, ulcerative colitis, constipation or diarrhea.

9. The method of claim 4, wherein the gastrointestinal disorder comprises inflammatory bowel disease, irritable bowel syndrome, Crohn's disease, ulcerative colitis, constipation or diarrhea.

10. The method of claim 6, wherein the gastrointestinal disorder comprises inflammatory bowel disease, irritable bowel syndrome, Crohn's disease, ulcerative colitis, constipation or diarrhea.

\* \* \* \* \*